United States Patent [19]
Sittler et al.

[11] Patent Number: 4,990,236
[45] Date of Patent: Feb. 5, 1991

[54] THIN FILM MOISTURE SENSING ELEMENT

[75] Inventors: Fred C. Sittler, Victoria, Minn.; Radhakrishna M. Neti, Brea, Calif.; Adrian C. toy, Eden Prairie, Minn.

[73] Assignee: Rosemount Inc., Eden Prairie, Minn.

[21] Appl. No.: 485,772

[22] Filed: Feb. 21, 1990

Related U.S. Application Data

[63] Continuation of Ser. No. 153,168, Feb. 8, 1988, abandoned.

[51] Int. Cl.⁵ .................................................. G01N 27/26
[52] U.S. Cl. ...................... 204/430; 73/335; 73/336.5; 204/153.22; 204/290 F
[58] Field of Search ............... 204/153.22, 430, 290 F; 73/335, 336.5

[56] References Cited

U.S. PATENT DOCUMENTS

| | | | |
|---|---|---|---|
| 3,001,918 | 9/1961 | Czuha | 204/430 |
| 3,133,872 | 5/1964 | Miller et al. | 204/290 F |
| 3,223,609 | 12/1965 | Reeds | 204/430 |
| 3,236,756 | 2/1966 | Beer et al. | 204/290 F |
| 3,313,721 | 4/1967 | Teel | 204/290 F |
| 3,337,441 | 8/1967 | Goldsmith | 204/430 |
| 3,954,590 | 5/1976 | Czuha | 204/430 |
| 4,280,885 | 7/1981 | Savery | 204/430 |
| 4,633,704 | 1/1987 | Tantram et al. | |
| 4,707,244 | 11/1987 | Harman, III et al. | 204/430 |
| 4,773,935 | 9/1988 | Uda et al. | 204/430 |

*Primary Examiner*—T. Tung
*Attorney, Agent, or Firm*—Kinney & Lange

[57] ABSTRACT

A solid state, thin film moisture sensing element is disclosed. The sensing element is fabricated by thin film deposition of at least a pair of two layer electrodes on an insulating surface. The active surface of the element is then coated with a layer of hygroscopic material and placed in a diffusion limiting housing to complete the sensing element assembly.

16 Claims, 5 Drawing Sheets

THIN FILM MOISTURE SENSING ELEMENT

This is a continuation of application Ser. No. 07/153,168 filed on Feb. 8, 1988, abandoned as of the date of this application.

BACKGROUND OF THE INVENTION

1. Field of the Invention.

This invention relates to electrolytic moisture sensing elements and more particularly to thin film moisture sensing elements and a process for the manufacture thereof.

2. Description of the Prior Art.

Various sensors for measuring the moisture content of a sample are known in the art. The various types of sensors and their basic principles of operation are described in a paper by Stanley Ronchinsky entitled "An Electrochemical Sensor for Trace Moisture in Gases," *Moisture and Humidity, Measurement and Control in Science and Industry*, 1985, pages 699 to 706. Of the different types of sensors described, the sensor type referred to as the "Electrolyzing Sensor" appears to be best suited for applications where continuous monitoring of moisture is required and for other industrial applications for the detection of trace amounts of moisture in samples.

Electrolytic sensors employ a moisture scavenger to trap the moisture in the sample and appropriate circuitry is provided to measure the amount of current required to electrolyze the resulting material. The operating principle of these sensors is Faraday's law of electrolysis in which the electrical charge required to electrolyze the material is a measure of the water content of the sample. Electrolysis is carried out by a pair or pairs of electrodes disposed in the body of the sensor.

The Keidel cell is an example of a moisture sensor operating on the electrolysis principle. Essentially the Keidel cell consists of a body which contains a pair of noble metal electrodes and which is packed with a suitable water scavenger such as phosphorous pentoxide. A sample stream is introduced into the body and the moisture is retained by the hygroscopic scavenger. The retained moisture is electrolyzed at the electrodes and the current required to electrolyze the moisture is measured. The Keidel cell and other forms of electrolytic sensors operating on the same principle require that the active area of the sensor be exposed to a constant flow of sample past the electrodes of the sensor. Variations in the sample flow rate can result in erroneous measurements and over time the hygroscopic scavenger tends to plug, causing a restriction in the flow of sample through the sensor and terminating the usefulness of the sensor. An alternative to this is to introduce a known volume of sample into the sensor and measure the total current over time required to completely electrolyze the moisture in the known volume of sample. This is time consuming and does not lend itself to use for continuous monitoring. In addition, sensors of the type described have slow response times to changes in the moisture content of the sample due to their bulkiness and are not sensitive over a wide range of moisture content.

Accordingly, it would be highly desirable to provide a moisture sensor which retains the accuracy and reliability of the electrolytic sensors and which is sensitive over a wide range of moisture content. In addition, it would be desirable to provide a moisture sensor which measures the moisture content of a sample independent of the flow rate or volume of the sample to which the sensor is exposed, thus rendering the sensor more useful for the measurement of moisture contained in a solid as well as in a fluid.

SUMMARY OF THE INVENTION

In accordance with the present invention, there is provided a solid state, thin film sensor for the determination of moisture content levels of a sample, comprising at least a pair of inert, conductive electrodes disposed on a structurally stable, electrically insulating surface. The electrodes are formed on the surface by thin film deposition techniques. The electrodes are spaced apart to define an interelectrode gap therebetween and a layer of hygroscopic electrolytic material such as phosphorous pentoxide is disposed over the electrode surfaces and in the interelectrode gap. The electrodes may be electrically connected to a source of electrical potential and current measuring instrumentation.

Silicon dioxide provides a preferred surface for the sensing element because of good insulating properties, lack of a moisture memory which would affect the element over time and its chemical inertness with respect to phosphoric acid, which is a product of a reaction between phosphorous pentoxide and water. Rhodium electrodes are indirectly bonded to the silicon dioxide surface by a titanium interface. Because titanium is subject to being corroded by phosphoric acid, however, the depth of the titanium interface is limited so that deposition of rhodium on top of the titanium results in a titanium-rhodium alloy at the surface of the substrate. Appropriate leads are then attached to the electrodes. Phosphoric acid is applied to the surface of the substrate over the electrodes and in the gaps between the electrodes. The acid is then dried to form a phosphrous pentoxide layer over the surface of the substrate and the electrodes. The element is set in a housing. The housing permits communication between the gases to be sampled and the sensing element. A diffusion limiting screen limits the moisture pressure adjacent the sensing element to a known fraction of the moisture pressure in the sample gas.

In operation, a moisture bearing gas is passed through the housing. A fraction of the water molecules pass through the diffusion limiting screen. Virtually all water molecules passing the diffusion limiting screen react with the hygroscopic electrolytic material to form an aqueous solution of phosphoric acid. The solution is electrolyzed at the electrodes to hydrogen, oxygen and phosphorous pentoxide. Any change in the moisture content of the sample gas results in a change in the diffusion rate across the diffusion limiter. This produces an increase or decrease in the rate at which the water molecules are being electrolyzed at the electrodes. The current required to carry out electrolysis likewise increases or decreases. In accordance with Faraday's law of electrolysis, the current change is directly related to the change in the moisture content of the sample. The current will continue to change until equilibrium conditions are established.

In accordance with the present invention, the sensor retains the convenience and reliability of conventional electrolytic sensors while exhibiting high sensitivity and rapid response to changes in moisture content of a sample. It is unnecessary to carefully control the flow of sample past the sensor and inaccuracies due to variations in the sample flow rate are avoided. By the same token, since the sensor of the invention does not require a continuous flow of sample to operate accurately, it is useful for the determination of moisture given off by solids and viscous fluids.

The advantages of a wide moisture range sensitivity and rapid response to changes in moisture content of a gas are obtained in part by radical reduction of the bulk mass of the sensing element. Such reduction in mass also increases the area to volume ratio of the element. Thin film metal deposition techniques developed for use in the fabrication of integrated circuits are adapted in the present invention for use in the fabrication of the sensing elements. The sensing elements fabricated are comparable in size to common integrated circuit dice.

DETAILED DESCRIPTION OF THE PREFERRED EMBODIMENTS

Figure 1:
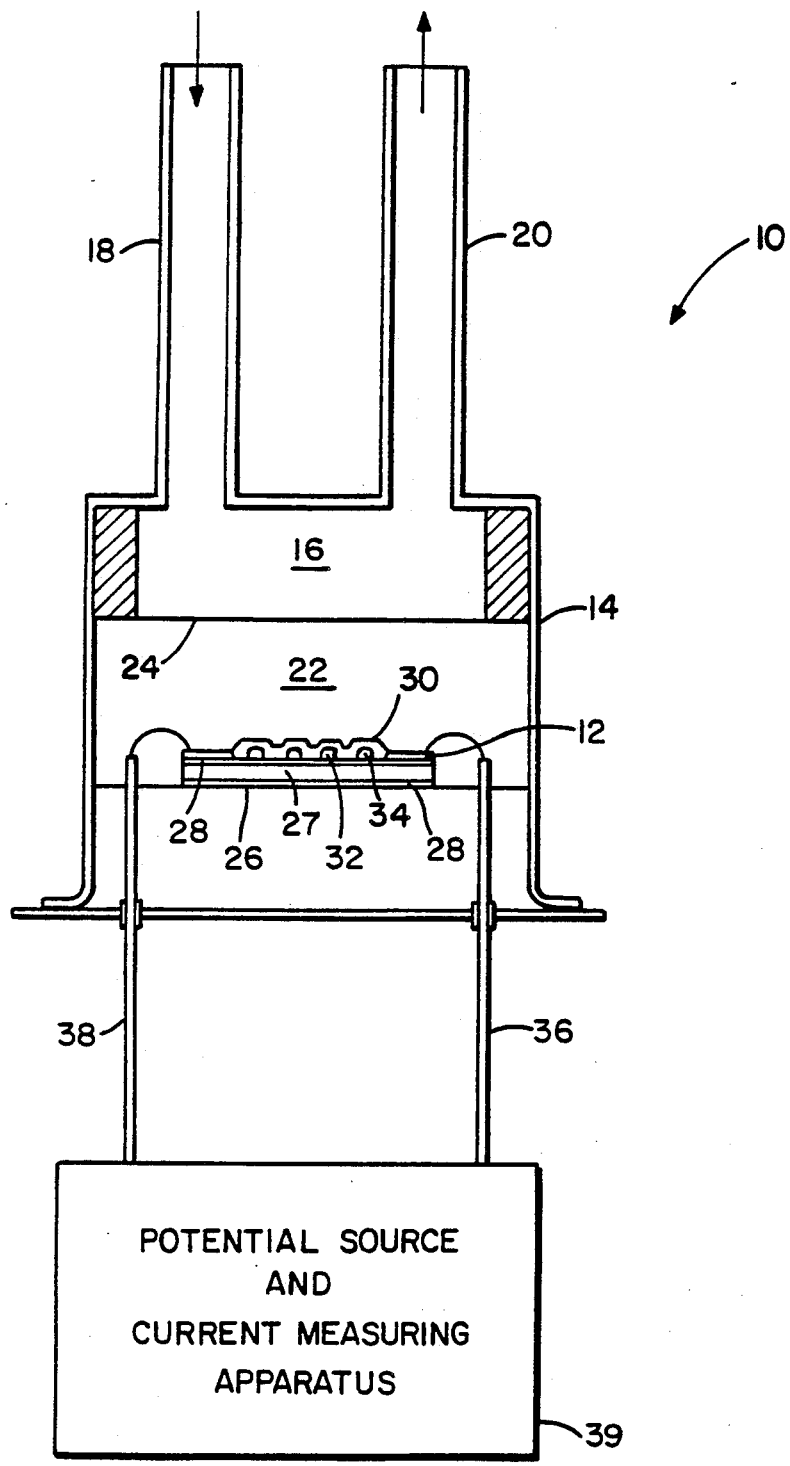
FIG. 1 is a cross sectional view of a moisture sensor assembly incorporating the moisture sensing element constructed in accordance with the invention.

FIG. 1 illustrates a moisture sensor assembly 10, comprising a substantially planar moisture sensing element 12. Moisture sensing element 12 is disposed within housing 14, which is preferably a conventional semiconductor or transistor can. Housing 14 is internally divided by diffusion limiting screen 24 into sample chamber 16 and sensing element chamber 22. Diffusion limiting screen 24 is preferably a stainless steel screen. A 1 to 100 micron screen can be selected to obtain diffusion limiting suited to the application environment, the housing and the sensing element geometry. A moisture bearing gas is introduced to sample chamber 16 by way of inlet 18 and is exhausted from sample chamber 16 by way of outlet 20. Inlet 18 and outlet 20 are preferably formed of a corrosion resistant material, for example, nickel. Diffusion limiting screen 24 reduces the moisture partial pressure in sensing element chamber 22 by nearly two orders of magnitude as against the partial pressure in sample chamber 16. The probability of absorption of water molecules reaching sensing element chamber 22 by element 12 becomes nearly 100%. Accordingly, the amount of moisture vapor absorbed becomes substantially independent of temperature. Diffusion across screen 24 is a linear function of the partial pressure of water vapor in sample chamber 16.

Moisture sensing element 12 is constructed on a substantially planar substrate 26. An insulating layer 28, formed of silicon dioxide grown from silicon layer 27 underlies the sensing element. In an alternative embodiment, substrate 26 may be a planar quartz substrate. Interdigitated electrodes 32 and 34 are disposed on the face of insulating substrate layer 28. Layer 28 and electrodes 32 and 34 are covered with a layer 30 of a hygroscopic material. Typically, hygroscopic layer is a layer 30 of phosphorous pentoxide which reacts with water molecules to form an aqueous solution of phosphoric acid which may be electrolyzed into molecular hydrogen, oxygen and phosphorous pentoxide by a potential imposed across electrodes 32 and 34. Hygroscopic layer 30 bridges the interelectrode gap between electrodes 32 and 34. Electrodes 32 and 34 may be connected across outside potential source and current measuring apparatus 39 by way of leads 36 and 38 which pass through the walls of housing 14.

Figure 2A:
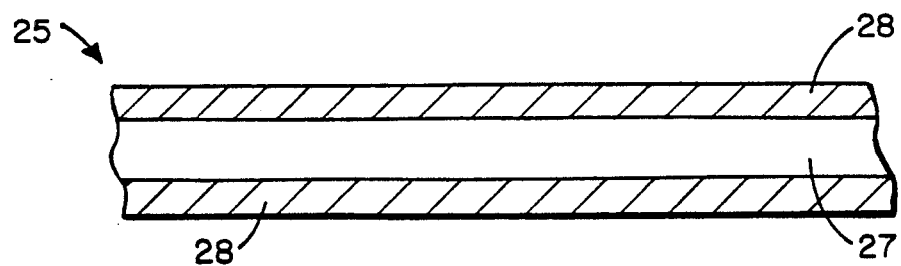
FIGS. 2A-H are cross sectional views of the sensing element in various stages of the process for the fabrication thereof.

FIGS. 2A-2H illustrate the steps of fabricating a moisture sensing element 12. FIG. 2A illustrates a silicon wafer 25 after oxidation of the outside surfaces of the silicon wafer in a high temperature oven with an oxidizing atmosphere. The oxidation step produces a wafer with a silicon substrate layer 27 and silicon oxide layer 28 which is in the range of 8000-12,000 angstroms and is preferably about 10,000 angstroms thick.

Figure 2B:
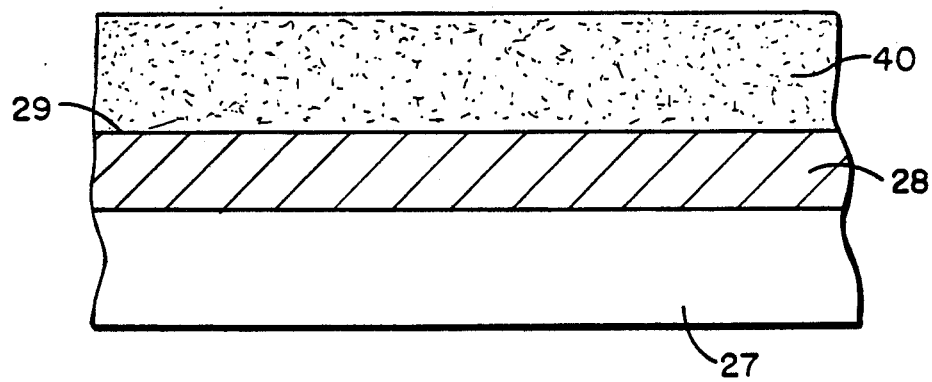

FIG. 2B illustrates selection of one silicon oxide layer 28 to provide an insulating surface 29 to support fabrication of the sensing element. A positive photoresist layer 40 is applied over insulating surface 29.

Figure 2C:
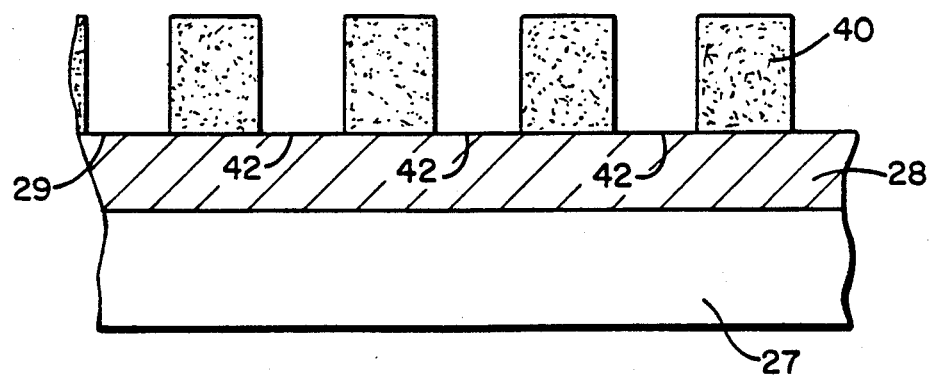

FIG. 2C illustrates the wafer after exposure and development to photoresist layer 40. Portions of photoresist layer 40 have been exposed to actinic radiation and developed, leaving openings in photoresist layer 40 exposing portions 42 of insulating layer 29. The pattern of exposed portions 42 define the location of electrodes which will be deposited on surface 29 of silicon dioxide layer 28.

Figure 2D:
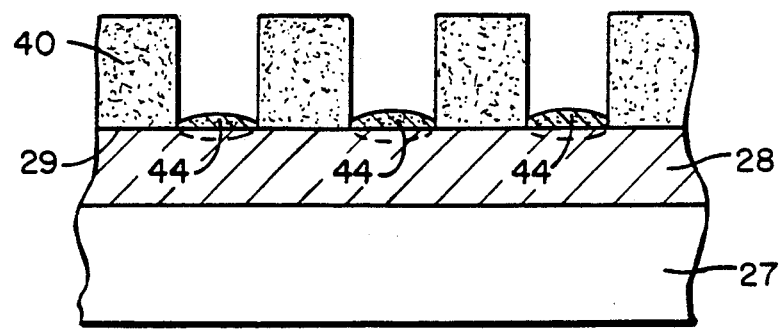

FIG. 2D illustrates deposition of a binding layer 44 on silicon dioxide layer 28 in the pattern of the electrodes to be formed. Binding layer 44 is preferably a layer of titanium of between 40 and 80 angstroms in depth. Other metals which would be suitable include chromium and nickel or such other material as suitably adheres to silicon dioxide. An electron beam is used to evaporate the titanium. A quartz oscillator control balance is used to ensure that the thickness of the titanium layer is carefully controlled, preferably averaging 50 angstroms. A portion of the titanium deposition penetrates silicon dioxide layer 28 and forms an alloy therewith.

Figure 2E:
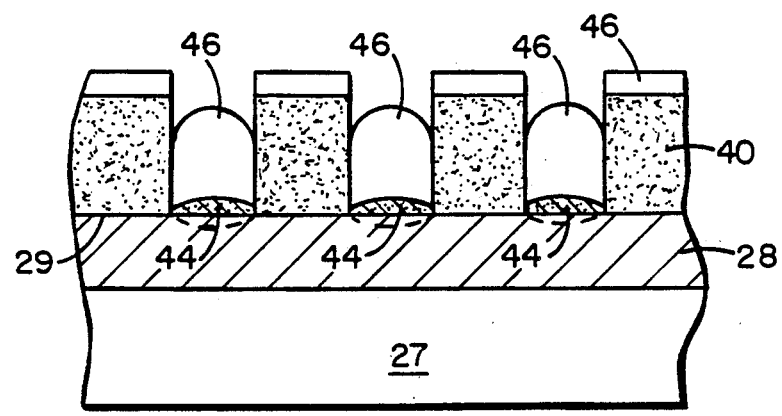

FIG. 2E illustrates deposition of metallic electrodes for the sensing element. Superior results are obtained if electrode layer 46 is deposited on titanium layer 44 immediately after deposition of layer 44. Electrode layer 46 is a noble metal, such as rhodium, platinum, or gold, but preferably rhodium. Rhodium electrodes 46 are in the range of 1,000-5,000 angstroms and average approximately 3,000 angstroms in depth. They are approximately 25 microns in width. Spacing between the interdigited finger of electrodes 46 is approximately 25 to 60 microns, with 40 microns being preferred. Deposition of rhodium electrodes 46 immediately after deposition of titanium binding layer 44 results in an alloy of the titanium and the rhodium. It is preferred that no pure titanium remain present, but that only blended alloys of titanium-rhodium and titanium-silicon oxide exist after deposition of the rhodium electrodes 46. This protects the titanium in binding layer 44 from attack by the phosphoric acid eventually applied to the device.

Figure 2F:
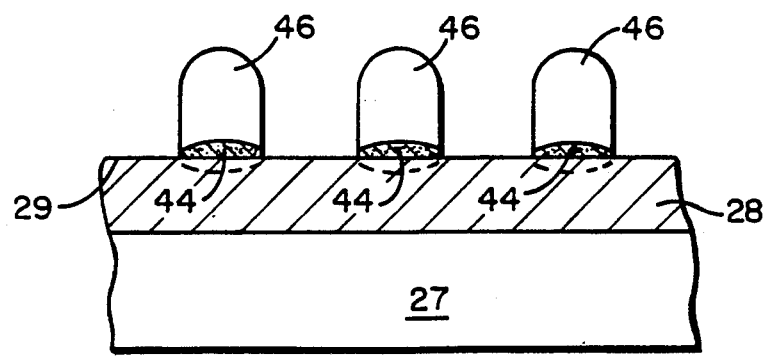

FIG. 2F illustrates removal of the unexposed positive photoresist layer 30 by washing the silicon wafer in an acetone bath.

Figure 2G:
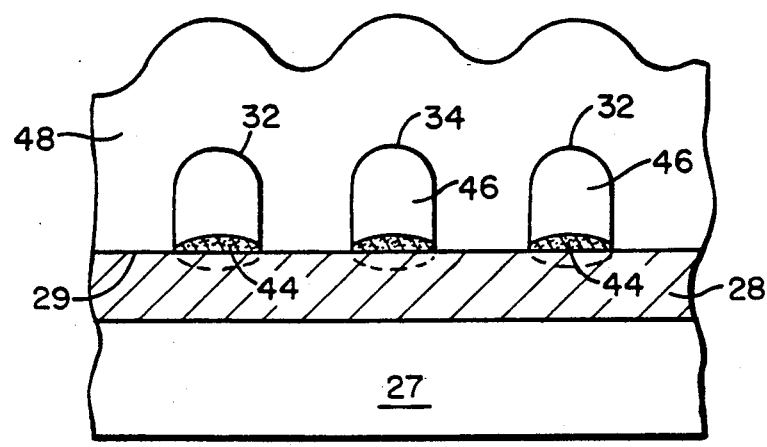

FIG. 2G illustrates application 48 of an aqueous solution of phosphoric acid to the surface of substrate layer 28, covering at least a portion of that layer and a plurality of electrode digits 32 and 34.

Figure 2H:
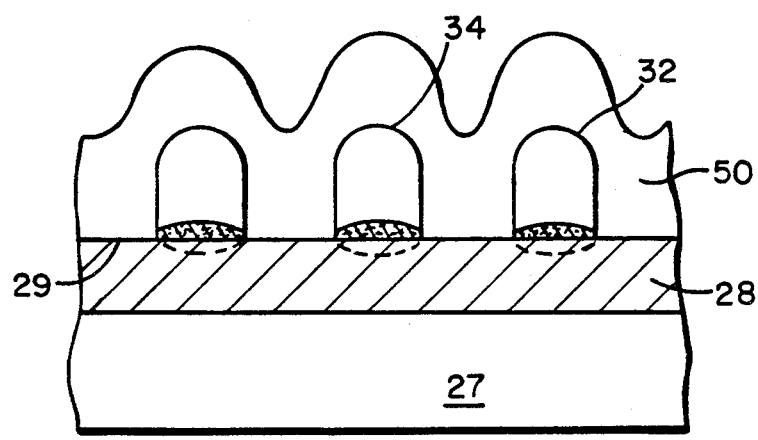

The aqueous solution is then dried, preferably by electrolysis, in a dry nitrogen atmosphere to form a phosphorous pentoxide layer 50 covering electrode digits 32 and 34 as illustrated in FIG. 2H and filling the interelectrode gap between digits 32 and 34.

Figure 3:
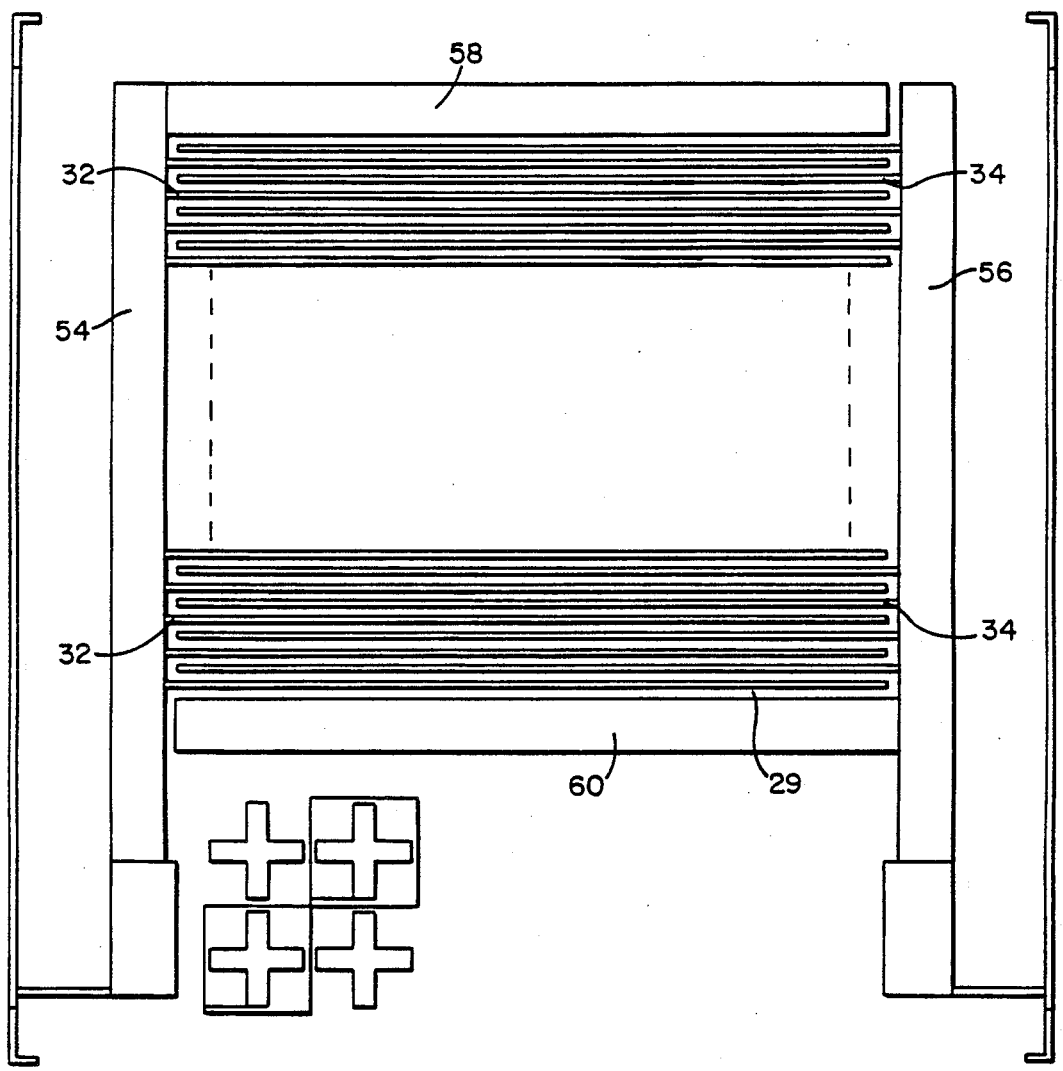
FIG. 3 is a plan view of the sensing element illustrating the electrodes disposed thereon in an interdigitated pattern.

FIG. 3 illustrates a plan view of sensing element 12 with interdigited electrodes 32 and 34. Electrodes 32 extend from pad 54 which is a part of rhodium deposition being of substantially greater width than electrode digits 32. Similarly pad 56 is a rhodiuum area of substantially greater width than digits 34. Rhodium pads 58 and 60 similarly extend from pads 54 and 56. Electrical leads may be attached to pads 54 or 58 and 56 or 60. Pads 54, 56, 58 and 60 define the active surface area of sensing element 12. Because rhodium is hydrophobic, an aqueous solution of phosphoric acid applied to insulating surface 29 remains within the lateral bounds of rhodium pads 54, 56, 58 and 60, if the width of the pads is sufficient. However, the width of electrode digits 32 and 34 is insufficient to prevent the spread of the aqueous solution across electrode digits 32 and 34.

In operation, the sensor assembly is connected across a voltage source and current measuring apparatus 39 by leads 36 and 38. Inlet tube 18 and outlet tube 20 may then be introduced to an environment to allow sampling of a gas to be analyzed for moisture content. As the moisture bearing gas enters chamber 16, its diffusion across stainless steel barrier 24 is limited as a function of the partial pressure of moisture in chamber 16. Moisture from the gas in chamber 22 is scavenged by the phosphorous pentoxide producing an aqueous solution of phosphoric acid in the interelectrode gaps between electrodigits 32 and 34. Current flow begins which may be measured and converted to an indication of water in terms of parts per million or billion by known mathematical relationships.

Thin film hygrometers constructed in accordance with the teachings of the present invention have proven capable of detecting moisture levels with a lower limit of 20 parts per billion in a sample gas. Actual devices have given accurate readings over temperature range of −30° C. to +70° C. The need for and the complexity of temperature compensation is reduced because the output signal is independent of sample gas flow. Independence from flow results from limiting diffusion into the chamber wherein the sensing element is actually disposed. Such independence also can allow the device to be used with respect to stagnant atmospheres, allowing moisture measurement of solids or viscous fluids. Placing a solid or viscous fluid in a closed environment with a dry gas will result in an equilibrium moisture level developing into the environment. The assembly of the present invention can then measure moisture level in the environment to provide an indication of the moisture content of the solid. The reduced size of the devices controls antenna effects and reduces noise interference substantially. Moisture level transistion response time has been shown to reach 63% of equilibrium in less than 5 minutes after the transition. This compares with a response time of an hour or more in prior art devices.

Although the present invention has been described with reference to preferred embodiments, workers skilled in the art will recognize that changes may be made in form and detail without departing from the spirit and scope of the invention.

What is claimed is:

1. A thin film moisture sensing element comprising:
a substantially planar surface layer of silicon dioxide;
at least two electrodes disposed on the surface layer, the electrodes being spaced to define an interelectrode gap therebetween;
each electrode including a noble metal layer and an alloy layer between the noble metal layer and the silicon dioxide surface layer, the alloy layer composed of a binding metal alloyed with the surface layer and the noble metal layer to bind them together, the alloy layer consisting essentially of alloys of the binding metal, the surface layer and the noble metal layer;
a hygroscopic material disposed in at least a first continuous layer over at least a portion of the surface layer and over portions of the two electrodes; and
means for electrically connecting the electrodes across a source of electrical potential and to electric current measuring instrumentation.

2. The sensing element as defined in claim 1 wherein the noble metal is selected from the group consisting of rhodium, platinum and gold.

3. The sensing element as defined in claim 1 wherein the alloy layer of the electrode is fabricated by depositing a layer of titanium not exceeding 80 Angstroms in thickness onto the silicon dioxide surface layer and immediately thereafter depositing rhodium onto the titanium.

4. The sensing element of claim 1 wherein the binding metal is selected from the group of binding metals consisting of titanium, nickel and chrome.

5. The sensing element of claim 1 wherein the alloy layer is no more than 80 angstroms thick and the noble metal layer is at least 1000 angstroms thick.

6. A moisture sensor assembly comprising:
a housing defining an enclosed chamber;
a diffusion limiting screen disposed within the enclosed chamber and dividing the enclosed chamber into sample chamber and a sensing element chamber;
inlet and outlet ports through the housing communicating with the sample chamber; and
a sensing element disposed within the sensing element chamber, the sensing element including:
a structurally stable, electrically insulating substrate having a silicon dioxide surface layer open to the sensing element chamber;
a pair of spaced electrodes disposed on the surface of the substrate, the electrodes comprising a layer of noble metal;
a continuous hygroscopic layer over a portion of the surface of the substrate and portions of each of the pair of electrodes; and
an alloy layer for each electrode alloyed between the noble metal electrode and the substrate surface layer, the alloy layer composed of a binding metal alloyed with the surface layer and the noble metal layer to bind them together, the alloy layer consisting essentially of alloys of the binding metal, the surface layer and the noble metal layer.

7. The moisture sensor assembly of claim 6 wherein the alloy layer is resistant to corrosive acid attack.

8. A thin film moisture sensing element, comprising:
a substantially planar silicon dioxide surface layer;
two electrodes, each electrode comprising:
an alloy layer formed of a binding metal alloyed with the planar surface; and
a noble metal layer, such that the alloy layer consists essentially of alloys of the planar surface, the binding metal and the noble metal, the electrodes selectively deposited to define an interelectrode gap therebetween;

a hygroscopic material contacting the two electrodes; and means for electrically connecting the electrodes across a source of electrical potential and to electric current measuring instrumentation.

9. The sensing element defined in claim 8 wherein the binding metal is selected from the group consisting of titanium, nickel and chromium.

10. The sensing element defined in claim 9 wherein the alloy layer is resistant to phosphoric acid attack.

11. The sensing element defined in claim 8 wherein the alloy layer is at least 25 times thinner than the noble metal layer.

12. The sensing element defined in claim 8 wherein the alloy layers are formed by depositing the binding metal by electron beam evaporation.

13. The sensing element defined in claim 8 wherein the noble metal is selected from the group consisting of rhodium, platinum and gold.

14. A thin film moisture sensing element, comprising:
a substantially planar silicon dioxide surface layer;
two electrodes, each electrode comprising:
an alloy layer not exceeding 80 angstroms in thickness on the planar surface;
a noble metal layer of at least 1,000 angstroms in thickness on top of the alloy layer;
the alloy layer consisting essentially of alloys of the material of the planar surface, a binding metal and the noble metal, and
the electrodes being selectively deposited to define an interelectrode gap therebetween
a hygroscopic material contacting the two electrodes; and
means for electrically connecting the electrodes across a source of electrical potential and to electric current measuring instrumentation.

15. The thin film moisture sensing element of claim 14 wherein the binding metal is selected from the group consisting of titanium, nickel and chromium.

16. The thin film moisture sensing element of claim 14 wherein the noble metal is selected from the group consisting of gold, platinum and rhodium.

* * * * *

UNITED STATES PATENT AND TRADEMARK OFFICE
CERTIFICATE OF CORRECTION

PATENT NO. : 4,990,236

DATED : February 5, 1991

INVENTOR(S) : Fred C. Sittler et al.

It is certified that error appears in the above-identified patent and that said Letters Patent is hereby corrected as shown below:

On the title page:
In [75] Inventors:, delete "toy", insert
--Toy--.

Col. 8, line 11, insert a ";" at the end of the line.

Signed and Sealed this

Twenty-eighth Day of July, 1992

Attest:

DOUGLAS B. COMER

Attesting Officer        Acting Commissioner of Patents and Trademarks